(12) United States Patent
Petrenko

(10) Patent No.: US 8,137,693 B2
(45) Date of Patent: Mar. 20, 2012

(54) DRUG DELIVERY NANOCARRIERS TARGETED BY LANDSCAPE PHAGE

(75) Inventor: Valery A. Petrenko, Auburn, AL (US)

(73) Assignee: Auburn University, Auburn, AL (US)

( * ) Notice: Subject to any disclaimer, the term of this patent is extended or adjusted under 35 U.S.C. 154(b) by 798 days.

(21) Appl. No.: 11/536,844

(22) Filed: Sep. 29, 2006

(65) Prior Publication Data

US 2007/0077291 A1    Apr. 5, 2007

Related U.S. Application Data

(60) Provisional application No. 60/722,320, filed on Sep. 30, 2005.

(51) Int. Cl.
*A61K 9/127*    (2006.01)
(52) U.S. Cl. .......................................... 424/450; 977/907
(58) Field of Classification Search .................... None
See application file for complete search history.

(56) References Cited

U.S. PATENT DOCUMENTS

| | | | |
|---|---|---|---|
| 5,965,710 | A | 10/1999 | Bodmer et al. |
| 6,117,632 | A | 9/2000 | O'Mahony |
| 6,413,544 | B1 * | 7/2002 | Smyth-Templeton et al. ............................. 424/450 |
| 6,589,727 | B1 | 7/2003 | Klenerman et al. |
| 2001/0006778 | A1 | 7/2001 | Benjamin et al. |
| 2002/0192675 | A1 | 12/2002 | Zauderer et al. |
| 2003/0068900 | A1 | 4/2003 | Belcher et al. |
| 2004/0005540 | A1 | 1/2004 | Petrenko et al. |
| 2004/0229215 | A1 | 11/2004 | Petrenko et al. |

FOREIGN PATENT DOCUMENTS

| | | |
|---|---|---|
| WO | 00/62351 A1 | 10/2000 |
| WO | WO 01/58910 A2 | 8/2001 |
| WO | 02/063280 A1 | 8/2002 |
| WO | 03/074548 A2 | 9/2003 |

OTHER PUBLICATIONS

Sapra et al. Progress in Lipid Res. 42:439-462; 2003.*
Petrenko et al. (Protein Eng. 13:589-592; 2000.*
Gabizon, Alberto et al. (2004) "Tumor Cell Targeting of Liposome-Entrapped Drugs With Phospholipid-Anchored Folic Acid-PEG Conjugates," Advanced Drug Delivery Reviews 56, p. 1177-1192.
Baluk, P., et al. (2005) "Cellular Abnormalities of Blood Vessels as Targets in Cancer," Current Opinion in Genetics & Development 15, pp. 102-111.
Brigati, J. et al. (2004) "Diagnostic Probes for Bacillus anthracis Spores Selected from a Landscape Phage Library," Clinical Chemistry 382, pp. 1346-1350.
Ceh, B., et al. (1997) Stealth® Liposomes: From Theory to Product Adv Drug Deliv Rev 24, pp. 165-177.
Il'ichev, A. et al. (1989) "Production of a Viable Variant of Phage M13 With Incorporated Foreign Peptide in the Major Envelope Protein," Doklady Biochemistry (ProAcad Sci Ussr)-Eng/Tr 307, pp. 196-198.

Jelinek, R. et al. (1997) "NMR Structure of the Principal Neutralizing Determinant of HIV-1 displayed in Filamentous Bacteriophage Coat Protein," Journal of Molecular Biology 266, 649-655.
Kataoka, K. et al. (2000) "Doxorubicin-loaded poly(ethylene glycol)-poly(beta-benzyl-L-aspartate)copolymer micelles: Their Pharmaceutical Characteristics and Biological Significance," J Control Release 64, pp. 143-153.
Petrenko, V.A. and V.J. Vodyanoy (2003) "Phage Display for Detection of Biological Threat Agents," Journal of Microbiol Meth 53, pp. 253-262.
Klibanov, A.L., et al. (1990) "Amphipathic Polyethyleneglycols Effectively Prolong the Circulation Time of Liposomes," FEBS Letters 268, pp. 235-237.
Lukyanov, A.N., et al. (2004) "Tumor-Targeted Liposomes: Doxorubicin-Loaded Long-Circulating Liposomes Modified with Anti-Cancer Antibody," J. Control Release 100, pp. 135-144.
Lukyanov, A.N. et al. (2004) "Micelles from Lipid Derivatives of Water-Soluble Polymers as Delivery Systems for Poorly Soluble Drugs," Adv Drug Deliv Rev 56, pp. 1273-1289.
McDonnell, P.A., et al. (1993) "fd Coat Protein Structure in Membrane Environments," Journal of Molecular Biology 233, pp. 447-463.
Monette, M. et al. (2001) "Structure of a Malaria Parasite Antigenic Determinant Displayed on Filamentous Bacteriophage Determined by NMR Spectroscopy: Implications for the Structure of Continuous Peptide Epitopes of Proteins," Protein Sci 10, pp. 1150-1159.
Moreira, J.N., et al. (2004) Antagonist G-mediated Targeting and Cytotoxicity of Liposomal Doxorubicin in NCI-H82 Variant Small Cell Lung Cancer. Braz J Med Biol Res 37, pp. 1185-1192.
Mount, J.D., et al. (2004) "Cell Targeted Phagemid Rescued by Pre-Selected Landscape Phage," Gene 341, pp. 59-65.
Nellis, D.F., et al. (2005) "Preclinical Manufacture of an anit-HER2 scFv-PEG-DSPE, Liposome-inserting Conjugate. 1. Gram-scale Production and Purification," Biotechnol Prog 21, pp. 205-220.
Nellis, D.F., et al. (2005) "Preclinical Manufacture of anti-HER2 Liposome-inserting, scFv-PEG-lipid Conjugate. 2. Conjugate Micelle Identity, Purity, Stability, and Potency Analysis" Biotechnol Prog 21, 221-232.
Olsen, E.V., et al. (2005) Affinity-selected Filamentous Bacteriophage as a Probe for Acoustic Wave Biodetectors of *Salmonella typhimurium*, Biosens Bioelectron in Press.

(Continued)

*Primary Examiner* — Michael Burkhart
(74) *Attorney, Agent, or Firm* — Andrus, Sceales, Starke & Sawall, LLP

(57) ABSTRACT

A targeted drug delivery nanocarrier and a method of forming the same is disclosed herein. The targeted drug delivery nanocarrier includes a plurality of amphipathic molecules forming a carrier particle having a plurality of drug molecules contained therein. A targeted landscape phage protein assembly is complexed to the carrier particle preferably using the unique method disclosed herein. The targeted landscape phage protein assembly displays a binding peptide that is selected to specifically and selectively bind to a target site. The method for forming targeted drug delivery nanocarriers includes the steps of obtaining a plurality of bacteriophage displaying a binding peptide for a desired target site, treating the bacteriophage with a denaturing agent, mixing the treated bacteriophage with a plurality of carrier particles and purifying the mixture to obtain a plurality of targeted drug delivery nanocarriers.

10 Claims, 5 Drawing Sheets

OTHER PUBLICATIONS

O'Shaughnessy, J.A. (2003) "Pegylated liposomal doxorubin in the treatment of breast cancer," Clin Breast Cancer 4, 318-328.

Petrenko, V.A., et al. (2005) "Nanofabrication of Bioselective Materials Using Diverse Nanolandscapes Displayed on Live Viruses," Proc. 2005 NSTI Nanotechnology Conference and Trade Show (Anaheim, California, U.S.A.).

Petrenko, V.A. and G.P. Smith (2000) "Phages from landscape libraries as substitute antibodies," Protein Engineering 13, pp. 589-592.

Petrenko, V.A. and G.P. Smith (2005) "Vectors and Modes of Display in Phage Display in Biotechnology and Drug Discovery" S.S. Sidhu, ed. (Bo Raton, FL, U.S.A., CRC Pressw, Taylor & Francis Group), pp. 714, 63-110.

Petrenko, V.A., et al. (2002) "Alphahelicaly constrained phage display library," Protein Engineering 15, pp. 943-950.

Petrenko, V.A. and I.B. Sorokulova (2004) "Detection of biological threat agents," Journal of Microbiological Methods 53, pp. 253-262.

Romanov, V.I., D.B. Durand, and V.A. Petrenko (2001) "Phage display selection of peptides that affect prostate carcinoma cells attachment and invasion," Prostate 47, pp. 239-251.

Sahoo, S.K., W. Ma, and V. Labhasetwar (2004) Efficacy of transferrin-conjugated paclitaxel-loaded nanoparticles in a murine model of prostate cancer, Int J Cancer 112, pp. 335-340.

Samoylova, T.I., et al. (2003) "Phage probes for malignant gilal cells," Molecular Cancer Therapeutic 2, pp. 1129-1137.

Smith, G.P., and V.A. Petrenko (1997) "Phage display," Chemical Reviews 97, pp. 391-410.

Sorokulova, I.B., et al. (2005) "Landscape phage probes for *Salmonella typhimurium*," J. Microbiol Methods 63, pp. 55-72.

Spruljt, R.B., C.J. Wolfs, and M.A. Hemminga (1989) Aggregation-related conformational change of the membrane-associated coat protein of bacteriophage M13, Biochemistry 28, pp. 9158-9165.

Torchilin, V.P. (2001) "Structure and design of polymeric surfactant-based drug delivery systems," J. Control Release 73, pp. 137-172.

Torchilin, V.P. (2005) "Recent advances with liposomes as pharmaceutical carriers," Nat. Rev. Drug Discov. 4, pp. 145-160.

Torchilin, V.P., et al. (2001) "p-Nitrophenylcarbonyl-PEG-PE-liposomes: fast and simple attachment of specific ligands, including monoclonal antibodies to distal ends of PEG chains via p-nitrophenylcarbonyl groups," Biochlm Biophys Acta 1511, pp. 397-411.

Torchcilin, V.P. et al. (2003) "Immunomicelles: targeted pharmaceutical carriers for poorly soluble drugs," Proc Natl Acad Sci USA 100 pp. 6039-6044.

Torchcilin, V.P. et al. (1996) "Poly(ethylene glycol)-coated anti-cardiac mysoin immunoliposomes: factors influencing targeted accumulation in the infarcted mycardium," Biochimica et Biophysica Acta (BBA)—Biomembranes 1279, pp. 75-83.

Kong, X.B. et al. (2005) "Intracellular delivery of doxorubicin with RGD-modified sterically stabilized liposomes for an improved anti-tumor efficacy: In vitro and in vivo," J. Pharm Sci 94, pp. 1782-1793.

Romanov, V.I. (2003) "Phage Display Selection and Evaluation of Cancer Drug Targets," Current Cancer Drug Targets, 3, pp. 119-129.

Mori, T. (2004) "Cancer-Specific Ligands Identified from Screening of Peptide-Display Libraries," Current Pharmaceutical Design, 10, pp. 2335-2343.

Schneider, Holm et al. (1998) "A novel peptide, Plaeidgielty, for the targeting of $\alpha9\beta1$-integrins," FEBS Letters, 429, pp. 269-273.

Petrenko, V.A. and G.P. Smith (2000) "Phages from landscape libraries as substitute antibodies," Protein Engineering, vol. 13, No. 8, pp. 589-592.

Dunker, A. Keith et al, "A Model for fd Phage Penetration and Assembly", FEBS Letters 10365, vol. 292, No. 1, 2, Nov. 1991, pp. 271-274.

Dunker, A. Keith et al, "Proposed Molten Globule Intermediates in fd Phage Penetration and Assembly", FEBS Letters 10366, vol. 292, No. 1, 2, Nov. 1991, pp. 275-278.

Petrenko, Valery A. and Smith, George P., "Phages from Landscape Libraries as Substitute Antibodies", Protein Engineering, vol. 13, No. 8, pp. 589-592, 2000.

Oh, Jeong S. et al, "Isolation of Chloroform-Resistant Mutants of Filamentous Phage: Localization in Models of Phage Structure", J. Mol. Biol. (JMB) (1999) 287, pp. 449-457.

Manning, Marcia et al, "Mechanism of Coliphage M13 Contraction: Intermediate Structures Trapped at Low Temperatures", Journal of Virology, vol. 40, No. 3, Dec. 1981, pp. 912-919.

Lopez, Javier and Webster, Robert E., "Minor Coat Protein Composition and Location of the A Protein in Bacteriophage f1 Spheroids and I-Forms", Journal of Virology, vol. 42, No. 3, Jun. 1982, pp. 1099-1107.

Griffith, Jack et al, "Filamentous Bacteriophage Contract into Hollow Spherical Particles upon Exposure to a Chloroform-Water Interface", Cell, vol. 23, Mar. 1981, pp. 747-753.

Roberts, Linda M. And Dunker, A. Keith, "Structural Changes Accompanying Chloroform-Induced Contraction of the Filamentous Phage fd", Biochemistry, vol. 32, No. 39, 1993, pp. 10479-10488.

Huang, Eva et al, "Surface Structure and Coverage of an Oligonucleotide Probe Tethered onto a Gold Substrate and Its Hybridization Efficiency for a Polynucleotide Target", Langmuir, vol. 17, No. 4, 2001, pp. 1215-1224.

Dultsev, F. N. et al, "Direct and Quantitative Detection of Bacteriophage by "Hearing" Surface Detachment Using a Quartz Crystal Microbalance", Analytical Chemistry, vol. 73, No. 16, Aug. 15, 2001, pp. 3935-3939.

Petrenko, Valery A. and Vodyanoy, Vitaly J., "Phage Display for Detection of Biological Threat Agents", Journal of Microbiological Methods, 53 (2003) pp. 253-262.

Uttenthaler, Erich et al, "Ultrasensitive Quartz Crystal Microbalance Sensors for Detection of M13-Phages in Liquids", Biosensors & Bioelectronics, 16 (2001) pp. 735-743.

Hengerer, Ame et al, "Quartz Crystal Microbalance (QCM) As a Device for the Screening of Phage Libraries", Biosensors & Bioelectronics, 14 (1999) pp. 139-144.

Kiefer et al., "Hydrophobic forces drive spontaneous membrane insertion of the bacteriophage Pf3 coat protein without topological control", The EMBO Journal, 1999, 18(22):6299-6306.

Soekarjo et al., "Thermodynamics of the Membrane Insertion Process of the M13 Procoat Protein, a Lipid Bilayer Traversing Protein Containing a Leader Sequence", Biochemistry, 1996, 35:1232-1241.

* cited by examiner

DRUG DELIVERY NANOCARRIERS TARGETED BY LANDSCAPE PHAGE

CROSS-REFERENCE TO RELATED APPLICATIONS

This application claims the benefit of Provisional Application No. 60/722,320 filed Sep. 30, 2005, entitled Drug Delivery Nanocarriers Targeted By Landscape Phage Proteins.

STATEMENT REGARDING FEDERALLY SPONSORED RESEARCH OR DEVELOPMENT

Not applicable.

BACKGROUND AND SUMMARY OF THE INVENTION

This invention relates to methods for treating various diseases, specifically cancer, using a targeted drug delivery nanocarrier that is selected to specifically and selectively bind to a target site. More particularly, this invention relates engineered tumor-targeted drug nanocarriers with controlled specificity, stability and high loading efficiency, suitable for the targeted intra-tumoral and intracellular delivery of pharmaceuticals.

Cancer is a group of diseases characterized by uncontrolled growth and spread of abnormal cells. If the spread is not controlled, it can result in death. Cancer is caused by both external factors (e.g. tobacco, chemicals, radiation and infectious organisms) and internal factors (inherited mutations, immune system conditions, the mutations that occur from metabolism). These causal factors may act together or in sequence to initiate or promote carcinogenesis. Currently, cancer is treated by surgery, radiation, chemotherapy, hormones and immunotherapy. However, there is an urgent need for more effective anti-tumor cancer drugs. For example, the life time risk for clinical prostate cancer is about 10% among U.S. men; approximately 3% die of this disease. Despite advances in early detection and treatment of the disease, the mortality rate has not declined, indicating that the current therapies are not adequate and new strategies are required.

The ideal anti-tumor therapy would enable the delivery of highly cytotoxic agent specifically to tumor cells and would leave normal cells unaffected. Conventional chemotherapeutic treatment, for example, with the agent doxorubicin, is limited because of the toxic side-effects that arise. The idea of drug targeting was first suggested by Paul Ehrlich more than 100 years ago. Recently, several approaches have been provided for the creation of tumor-targeted drugs.

One approach utilized conjugates of tumor-cystic probes with toxins, McCune et al., Journal of the American Medical Association 286, 1149-1152 (2001); Wahl, et al. Int. J. Cancer 1993, 590-600 (2001). For example, monoclonal antibodies or growth factors, such as epidermal growth factor (EGF) were conjugated to various toxins including pseudomonas or diphtheria toxins, which arrest the synthesis of proteins and cells, see, e.g., FitzGerald and Pastan, Journal of the National Cancer Institute 81, 1455-1463 (1989). However, the disadvantage of this type of system is that it may provoke an immune system reaction due to the non-human components, which decreases the effectiveness of the treatment and may result in a suppression of the immune system. Additionally, the drug conjugates are subject to elimination from the circulation through renal filtration, and schematic degradation, uptake by the reticuloendothelial system (RES) and accumulation in non-targeted organs and tissues.

Another approach takes the advantage of the hyper-permeability of vascular endothelia at tumor sites by using passive drug carriers, such as polymers, see e.g. Kostarelos and Emfietzoglou, Anti Cancer Research 20, 3339-3345 (2000); Matsumura and Maeda, Cancer Research 46, 6387-6392, (1986); and Thanou and Duncan, Curr. Opin. Investig. Drugs 4, 701-709 (2003). Other passive drug carriers suggested by the literature included liposomes and polymeric micelles, Duncan et al., J. Control Release 74, 135-146 (2001); Husseini et al., J. Control Release 83, 303-305 (2002); Kataoka et al., J. Control Release 64, 143-153 (2000); Rapoport et al., J. Control Release 91, 85-95 (2003). Matsumura and Maeda, cited above, observed that polymeric drugs and macromolecules accumulate within solid tumors due to an enhanced permeability and retention mechanism. The enhanced permeability and retention mechanism is based on characteristics of solid tumors such as high vascular density, reduced lymphatic drainage, extensive production of vascular mediators and defects in vascular structure.

Accordingly, "magic shells" of individual drug molecules packed into targeted carriers that protect the drug molecules from inactivation in an aggressive biological environment and improve drug delivery to the site of disease are considered the state of the art in drug delivery systems. In order to perform its mission and affect cancer cells in a tumor, a blood-borne therapeutic particle must travel into the blood vessels of the tumor, pass across the vessel wall into the interstitium, migrate through the interstitium, and unload its cargo into the tumor cells. Organ or tissue accumulation may be achieved by the passive targeting via the enhanced permeability and retention of the tumoral tissue or by active probe-mediated targeting. Intracellular delivery may be mediated by cell-recognizing and penetrating ligands.

The concept of targeted drug nanocarriers has stimulated tremendous research efforts and resulted in designs of new carrier particles, such as micelles, liposomes, capsules, spheres, etc. and their conversion into physiologically acceptable and stable drug carriers, Torchilin, Nat. Rev. Drug Discov. 4, 145-160 (2005); Churchland et al., Proc. Nat'l. Acad. Sci. USA 100, 6039-6044 (2003). Micelles and liposomes will be further discussed, herein. Despite the recent advances, there are still some physiological barriers in realizing the concept of targeted drug carriers. These barriers include fast clearance of foreign particles from the blood, and technological hindrances in obtaining highly standardized, pharmaceutically acceptable multi-functional nanoparticles. The biggest challenge, however, is that particles are still mostly administered through circulation. In order to stimulate accumulation of the drug loaded nanocarriers at the target site, the nanocarriers should be supplied with specific probes capable of binding the target tumor cells. Such nanocarriers need to have longevity and target recognition. Attempts have been made to conjugate micelles and liposomes with water soluble polymers and target specific probes. However, the majority of these particles are still cleared through circulation because the probes lack the specificity and selectivity necessary for high efficacy in administration of the drug to the target site.

The size and surface properties of the carrier particles are of crucial importance in achieving controlled drug delivery. Ideally, carrier particles should be small biodegradable particles with good loading capacity, prolonged circulation, and ability to accumulate in required areas. These requirements are reasonably well-met by micelles and liposomes, which are well-known in the art for use in poorly soluble and water-soluble drugs.

Micelles are self-assembling spherical colloidal nanoparticles formed by amphiphilic molecules. Micelles are also described as aggregate surfactant molecules disbursed in a liquid colloid. As demonstrated in FIG. 1, hydrophobic fragments 1 of amphiphilic molecules form the core of a micelle while their hydrophilic heads 3 form a micelle corona. The core of the micelle, which is segregated in an aqueous milieu, is capable of encapsulating drugs protecting them from destruction and biological surroundings while improving their pharmacokinetics and biodistribution. Micelles are generally in the order of 5-50 nm in diameter, and are therefore capable of accumulating in pathological areas with leaky vasculature, such as infarct zones and tumors due to the enhanced permeability and retention effect. Micelles are also capable of evading a major obstacle in drug targeting by particulate systems: non-specific uptake by the reticulo-endothelial systems and renal secretion.

Micelles may be formed by any of commonly known surfactants, such as sodium dodecylsulfate or phospholipids, but the performance of such surfactants as drug delivery systems is low compared to micelles composed of specially designed block copolymers, as described in Kataoka et al., supra and Torchilin et al., supra (2003). The flexible hydrophilic polymers, which are used as shell-forming segments for the polymer micelles, assemble into a dense palisade shell, which is cross-linked by numerous water molecules to achieve effective stabilization of the vesicle. Accordingly, the polymer micelles dissociate much more slowly than unmodified surfactant micelles, retain the loaded drugs for a longer period of time and accumulate the drug at the target site more efficiently. Further, polymer micelles are readily engineered to have sizes in the range of several tens of nanometers with a narrow size distribution which is a great advantage in regulating biodistribution.

In contrast to micelles, liposomes are a bilayered phospholipid vesicles approximately 50 to 1,000 nm in diameter. As shown in FIG. 2, liposomes can carry a variety of water soluble and water insoluble drugs loaded in an inner aqueous compartment 2 or into the phospholipid bilayer 4. Liposomes are biologically inert and completely biocompatible; they cause practically no toxic or antigenic reactions. Drugs included into liposomes are protected from the destructive action of the external media by the liposomes. Thus, liposomes are able to deliver their content inside cells and even inside different cell compartments. Water-soluble drugs can be captured by the inner aqueous compartment of liposomes, whereas lipophilic compounds can be incorporated into the phospholipid bilayer. Like drug loaded micelles, drug loaded liposomes rely on passive targeting and the enhanced permeability and retention effect that allows for the accumulation of anti-cancer drugs in the solid tumors without affecting normal tissues. The differential accumulation of micelle and liposomal drugs in tumor tissues relative to normal tissues is the basis for increased tumor specificity relative to free drugs. Accordingly, liposomes are considered a promising drug carrier with significant therapeutic potential, as demonstrated in numerous laboratory tests and clinical trials, e.g., Torchilin, Nat. Rev. Drug Discov. 4, 145-160 (2005).

It is known that liposomes and micelles can be stabilized by enhancing the outermost hydrophobic shell with water soluble polymers, such as polyethyleneglycol (PEG). The presence of hydrophilic polymers on the hydrophobic surface of these carrier particles attracts a water shell, resulting in reduced adsorption of opsonins to the carrier particles. This, in turn, results in a decrease in both the rate and extent of uptake of carrier particles by mononuclear phagocytes. Long circulating liposomes improved the therapeutic index of drugs and encapsulated therein. Currently, several preparations based on long circulating liposomes are commercially available, for example, Doxil®, a doxorubicin containing polyethyleneglycolated (PEGylated) liposomes, Sharp et al., Drugs 62 2089-2126 (2002). Doxil is manufactured by Ortho Biotech Products, LP of Bridgewater, N.J., USA. O'Shaughnessy, Clin. Breast Cancer 4, 318-328, (2003), demonstrated selective delivery of doxorubicin into solid tumors in patients with breast carcinoma metastases was achieved by capsulation of the drug into PEGylated liposomes, which resulted in subsequent improvement of survival. Efficacy was also demonstrated by combining liposomal doxorubicin with paclitaxel (available as Taxol®, Bristol-Meyers Squibb Company, New York, N.Y., USA) caelyx (Schering-Plough Corporation, Kenilworth, N.J., USA) and carboplatin (available as Paraplatin® from Bristol-Meyers Squibb Company). Several preparations of liposomes have been approved for clinical application or undergoing clinical evaluation, Torchilin, supra, (2005).

It is also known in the art to encapsulate antibiotic and antibacterial drugs within carrier particles such as micelles or liposomes. Moreover, it is known in the art to include therapeutically active polynucleotides, e.g., RNA, DNA, cDNA, mRNA, etc., into liposomes for protected administration.

One of the distinct drawbacks of liposome and micelle preparations injected intravenously for systemic application is their fast elimination from the blood because of their capture by the cells of the reticulo-endothelial system, primary the liver. As aforementioned, this problem was first addressed by adhering water soluble polymers to the carrier particles' outer shell. Another solution is to target the effected organ or tissue by coupling the loaded carrier particle with ligands capable of recognizing and binding to cells of interest.

In order to achieve more specific targeting of carrier particles, such particles are modified with various ligands using advance conjugation procedures. For example, antibodies and small peptides have been attached to the water exposed tips of polyethyleneglycol chains, Blume, et al. Biomembranes 1149, 180-184 (1993). Antibodies and small peptides have also been conjugated via reactive p-nitrophenylcarbonyl, N-benzotrazole carbonyl or maleimide terminated PEG-phosphatidylethanolamine, Moreira, Pharm. Res. 19, 265-269 (2002); Torchilin et al., supra (2001); Xiong, et al., J. Pharm. Sci. 94, 1782-1793 (2005). These conjugation procedures, which are adapted from the arsenal of organic chemistry, are effective for the preparation of various targeted carrier particles on a small scale basis, i.e., for preliminary laboratory and clinical studies, it would be significantly less efficient when moved to large scale preparation where standardized pharmaceutically acceptable preparations will be required. For example, it was noted in the most advanced recent studies, Nellis, et al., Biotechnol. Prog. 21, 205-220 (2005), that the largest 40-L culture produced enough of F5cys to manufacture 2,085 mg of conjugate, enough to support planned pre-clinical and future clinical trials. This extremely laborious procedure, including high volume propagation of bacteria, several chromatographic steps for producing the targeted ligand, sophisticated conjugation procedure and further chromatographic purification of the conjugated lipid moiety, yields a conjugate with only 93% purity. Obviously, this would be inefficient and highly cost expensive at the production stage.

Thus, despite its promise, targeted carrier particle technology is not without difficulties. Preparation of the targeting ligands, such as antibodies, and their conjugation to the lipids to make usable quantities of the targets of carriers has proven troublesome, differing idiosyncratically from one targeted particle to another. Accordingly, there is a need for an easily assembled targeted carrier particle that has efficient assembly/conjugation, little bioreactivity and specificity and selectivity in binding target sites.

To respond to the challenge of drug targeting, targeting technologies are being revolutionized by utilizing methods of combinatorial chemistry and phage display. The present inventor and colleagues have developed a phage display library where targeted peptides or antibodies are selected from billion clone phage display libraries and then expressed in bacteria or chemically synthesized to obtain a desired bioselective material, Petrenko and Sorokulova, Journal of Microbiological Methods 58, 147-168 (2004); Smith and Petrenko, Chemical Reviews 97, 391-410 (1997).

Phage-display libraries refer to a selection technique wherein a library of variants of a peptide or protein is expressed on the outside of a phage virion, while the genetic material encoding the peptide or protein remains inside the phage. Phage-display libraries are constructed by the genetic modification of filamentous bacterial viruses (phages) such as M13, fl, and fd. Referring now to FIG. 3, these bacteriophages are lengthy, their virions consisting of single stranded circular DNA packaged in a cylindrical shell of a major coat protein pVIII. The outer coats of these filamentous phages are composed of thousands of α-helical subunits of major coat protein pVIII which form a tube encasing the viral DNA. At the tips of the phage are several copies of each of the minor proteins, pIII, pVI, pVII, and pIX. To create a phage-display library, degenerate synthetic oligonucleotides are spliced in-frame into one of the phage coat protein genes, so that the peptide encoded by the degenerate oligonucleotide is fused to the coat protein and thereby displayed on the exposed surface of the phage virion. Accordingly, each phage virion displays multiple copies of one particular peptide.

Referring now to FIG. 4, in landscape phages, as in traditional phage-display constructs, foreign peptides or proteins 5 are fused to coat proteins 7 on the surface of the virus particle. Unlike conventional phage constructs, however, landscape phages display thousands of copies of the peptide 5 in a repeating pattern, comprising a major fraction of the viral surface. The phage body serves as an interacting scaffold to constrain the peptide into a particular confirmation, creating a defined organic surface structure, i.e., the landscape. The particular conformation, and thus organic surface structure, varies from one phage clone to the next Accordingly, a landscape phage library is a huge population of such phages, encompassing billions of clones with different surface structures and biophysical properties.

The major coat protein pVIII is a typical membrane protein. During infection of a host, e.g., $E.\ coli$, with the filamentous bacteriophage, the coat is dissolved in the bacterial cytoplasmic membrane, while viral DNA enters the cytoplasm. Protein is synthesized in the infected cell as a water soluble cytoplasmic precursor, which contains an additional leader sequence of 23 residues at its N-terminus. When this protein is inserted into the membrane, the leader sequence is cleaved off by a leader peptidase. Later, during the page assembly the newly synthesized major pVIII proteins are transferred from the membrane into the coat of the emerging phage. The structural flexibility of major coat protein is determined by its unique architecture. Thus, the major coat protein pVIII can change its confirmation to accommodate various distinct forms of the phage and its precursors: phage filament, intermediate particle form (I-form), spheroid form (S-form), and membrane bound form.

The ability of the major protein pVIII to become associated with micelles and liposomes emerges from its intrinsic function as a membrane protein. The structure of major coat protein pVIII in micelles and bilayer membranes is well resolved. A 50 amino acid long pVIII protein is very hydrophobic and insoluble in water when separated from virus particles or membranes. In virus particles, it forms a single, distorted α-helix with only the first four to five residues mobile and unstructured. It is arranged in layers with a five-fold rotational symmetry and approximately two-fold screw symmetry around the filament access, as demonstrated in FIG. 5.

Still referring to FIG. 5, in the membrane bound form of the pVIII protein, the 16-Å-long amphipathic helix 6 (residues 8-18) rests on the membrane surface 8, while the 35-Å-long trans-membrane helix 10 (residues 21-45) crosses the phospholipid bilayer 12 at an angle of 26° up to residue Lys40, where the helix tilt changes. The helix tilt accommodates the thickness of the phospholipid bilayer, which is 31 Å for $E.\ coli$ membrane components.

Liposomes displaying coat protein pVIII fixed in the lipid bilayers have heretofore been prepared by sonification of the virus with excess of phospholipids, such as DMPC (dimyristoyl-sn-glycero-phosphocholine). It is also known that the pVIII protein can be reconstituted into phospholipids through a dialysis process, yielding liposomes with a lipid to protein ratio of approximately 250.

Micelle forms of the pVIII can be obtained by its complexing with different lipids, such as sodium dodecyl sulfate, dodecyl phosphatidyl choline, dihexanoyl phosphatidyl choline or lyso myristoyl phosphatidyl choline. In the micelles, like liposomes, the pVIII protein forms two α helixes connected by a hinge, amphipathic 9-mer helix (residues 8-16) accommodated in the plane of the bilayer and an 18 residue trans-membrane hydrophobic helix (residues 27-44) spans the micelle. The N and C terminal regions of the membrane protein pVIII are mobile, although the C terminus may also be involved in the helical structure. The amphipathic helix has significantly more motional freedom than the hydrophobic helix and moves on and off the micellar surface.

The instant disclosure combines the advantages of liposomes and micelles as drug delivery systems with the unique ability of landscape phages to specifically and selectively bind target sites. The inventors have developed a novel way of combining pVIII fusion phages with micelles and liposomes wherein the pVIII fusion phages display a guest peptide in every pVIII subunit.

Accordingly, a targeted drug delivery nanocarrier is provided, the nanocarrier comprising a plurality of amphipathic molecules, a targeting landscape phage and a plurality of drug molecules. The amphipathic molecules form a carrier particle having the plurality of drug molecules contained therein and the targeting landscape phage is complexed to the carrier particle. The targeting landscape phage displays a binding peptide selected to specifically and selectively bind to a target site. The desired carrier particle may be either a micelle or a liposome, or another similar, related particle. The landscape phage is preferably a filamentous landscape phage. More preferably, landscape phage is a filamentous landscape phage that displays the binding peptide in major coat protein pVIII.

The invention also contemplates a method for forming a targeted drug delivery nanocarrier. The method comprises the steps of obtaining a plurality of bacteriophage displaying a binding peptide for a desired target site, treating the plurality of bacteriophage with a denaturing agent, mixing the treated bacteriophage with a plurality of carrier particles, and purifying the mixture to obtain a targeted drug delivery nanocarrier. The denaturing agent is preferably chloroform; however, any suitable denaturing agent may be used. It is important that the denaturing agent convert the filamentous bacterial phage into a spheroid (S-form) conformation. The carrier particle is preferably a micelle or liposome, but may be any suitable carrier particle that is readily mixed with treated bacteriophage. Finally, the step of purifying preferably comprises purifying the mixture through filtration chromatography; however, any type of purifying wherein the drug delivery or nanocarriers are separated from contaminants in the mixture is acceptable according to the method of the present invention.

DETAILED DESCRIPTION

Figure 1:
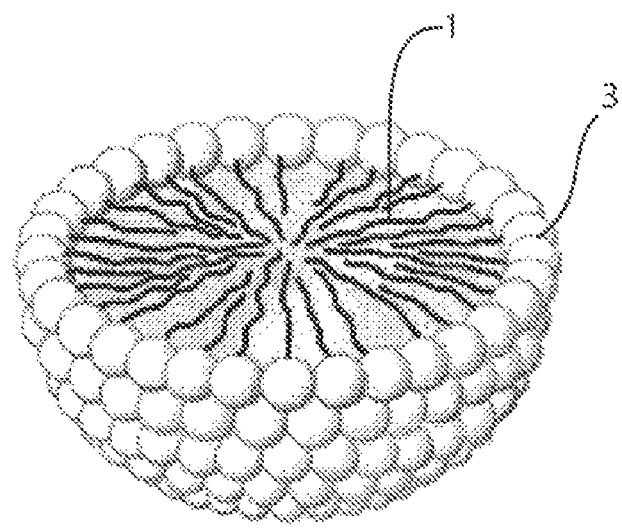
FIG. 1 is a schematic demonstrating the structure of a micelle, in which hydrophobic fragments 1 of amphiphilic molecules form the core of a micelle while their hydrophilic heads 3 form a micelle corona.
Figure 2:
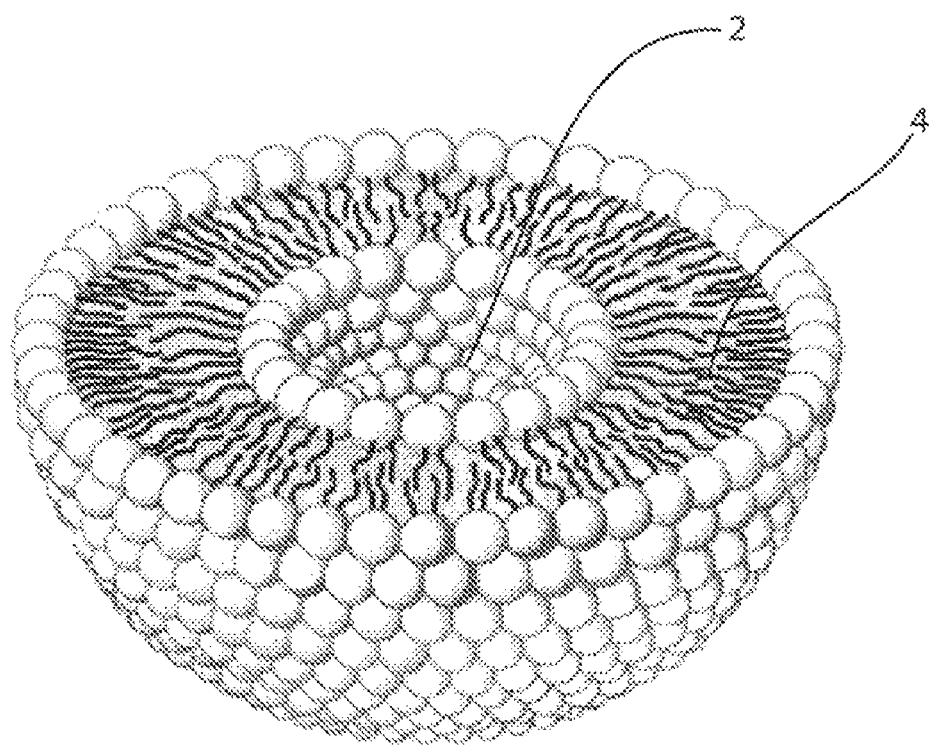
FIG. 2 is a schematic demonstrating the structure of a liposome, which can carry a variety of water soluble and water insoluble drugs loaded in an inner aqueous compartment 2 or in the phospholipid bilayer 4.
Figure 3:
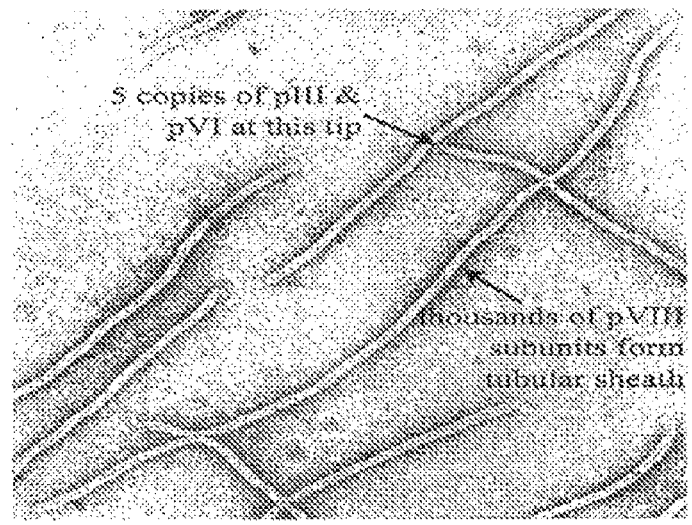
FIG. 3 is an electron micrograph of a filamentous phage demonstrating the location of the major coat protein pVIII.
Figure 4:
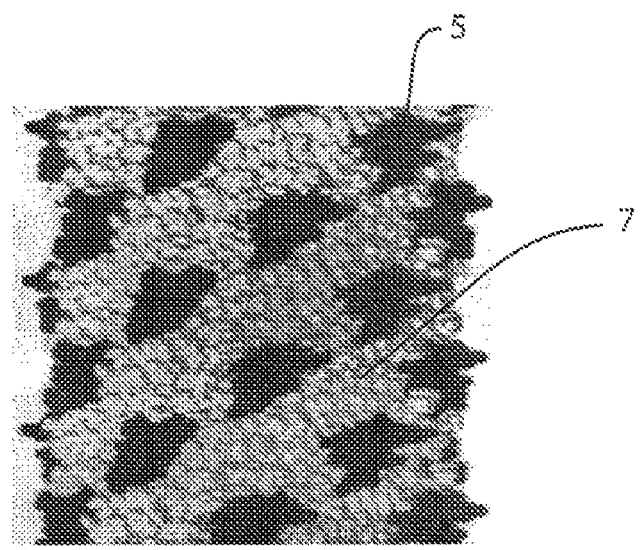
FIG. 4 is a computer model of a short length of an f8-1 landscape phage displaying guest peptides in a major coat protein pVIII wherein the inserted peptides 5 are shown as dark atoms and the wild-type peptides 7 are shown as light atoms.

The present application is directed to a new approach to targeted drug delivery nanocarriers and relies on a novel method using a treated or stripped landscape phage as the targeting probes of drug loaded carriers such as liposomes and micelles. The phage specific for the target organ, tissue or cell is selected from a multi-billion landscape phage library as described in Mount et al, Gene 341, 59-65 (2004); Romanov et al, Prostrate 47, 239-251 (2001); Romanov et al, Cancer Res. 64, 2083-2089 (2004); and Samoylova et al, Molecular Cancer Therapeutic 2, 1129-1137 (2003). The selected landscape phage is then treated with a denaturing agent, such as chloroform, and is converted to the carrier particle using the intrinsic membrane associated properties of the phage proteins. As a result, the targeting probe 6, i.e., the tumor specific peptide fused to the end terminus of the major coat protein pVIII, is exposed on the shell of the drug loaded carrier particle, as demonstrated in FIG. 5.

In contrast to the poorly controlled conjugation procedures known for coupling peptides and antibodies to the carrier particles, the new landscape phage based approach relies on the very powerful and extremely precise mechanisms of selection, biosynthesis and self-assembly. Furthermore, the subject matter of the present application does not require idiosyncratic reactions with any new shell associated polymer or targeting ligand and may easily be adapted to a new phage particle composition or a new addressed target site. No re-engineering of the selected phage is required; phage themselves serve as the source of the final product as the pVIII major coat protein comprising the body of the phages is genetically fused to the targeting peptide.

Moreover, the culture of cells creating filamentous phage is an efficient, convenient and discontinuous protein production system. The yield of wild-type particles regularly reaches 300 mg per liter, and yield for engineered landscape phages, as described herein, is approximately 20 mg per liter. Further, purification of the secreted proteins is easily accomplished by simple, routine steps that do not differ from one clone to another. More significantly, the major coat protein constitutes 98% of the total protein mass of the filamentous bacteriophage, purity hardly obtainable in normal synthetic or bioengineering procedures. Furthermore, the phage itself and its components are not toxic and have been routinely tested for safety in preclinical trials.

It is known in the art that landscape phages operate as substitute antibodies; however, landscape phages have much higher specificity and selectivity binding to target sites. Landscape phages were explored first as substitute antibodies using model antigens: streptavidin from *Streptomyces avidinii*, avidin from chicken egg white, bovine fibrinogen and β-galactosidase from *E. coli*. Binding of the selected phage to their target antigens was characterized by enzyme linked immuno sorbent assay (ELISA) and by quartz crystal microbalance (QCM) in which immobilized phages reacted with their antigens in solution phase. These tests demonstrated specific dose-dependent binding of each antigen to the phage it selected. Competition ELISAs and QCM measurements verified also that non-immobilized peptide-bearing phage, as well as stripped phage proteins and their synthetic version, compete with immobilized phage for binding to their respective antigens, Petrenko et al, Prot. Eng. 13(8): 589-592 (2000). Experiments with different antigens have shown that landscape phages and their stripped proteins may be used as substitute antibodies that bind protein and glycoprotein antigens with nanomolar affinities and high specificity. Isolated phages that bind strongly and specifically to complex biological agents, e.g., live bacterial and tumor cells, have been identified, Petrenko et al, Phage As Biospecific Probes, in Immunoassay and other Bioanalytical Techniques, J. M. V. Emon, Editor. 2006, CRC Press, Taylor & Francis Group: Boca Raton, Fla., U.S.A.

For example and without limitation, specific ligands to LNCaP and C4-2B prostrate carcinoma cell receptors have been isolated from a landscape phage library. The selected phages and cognate peptides were shown to interact specifically with the tumor cells affecting their cancer-related functions, such as adhesion, spreading, motility and invasion. One of the selected phages blocked spreading of LNCaP cells and their derivatives C4-2 and C4-2B. Cognate peptides did not inhibit spreading, but instead promoted binding of C4-2 and C4-2B cells to endothelial cells and activated matrix metalloproteinase (MMP)-2 and -9 in such cells. These results indicate that the identified ligands interact with functionally important and cancer related receptors of tumor cells linked to tumor generation and metastatic transformation.

As a further example and again without limitation, the inventor selected phages that bind to RG2 rat glioma cells from a landscape phage library using unbiased and biased selection schemes. In the first scheme, rat glial cells RG2 were treated with the phage library containing all initial repertoire of the random clones, except the clones binding to the plastic of the culture flask. The cell binding and penetrating phage was then extracted separately by acid and deoxycholate buffers. This extraction procedure allows for isolation of phages which bind to the most abundant receptors of the target cells, although not necessarily cancer specific. Indeed, phage selected by this protocol demonstrated limited selectivity towards glioma cells in comparison with normal rat astrocytes, myoblasts, hepatocytes and fibroblasts. Moreover, in advanced selection schemes, the library was first depleted against various normal cells (e.g., fibroblasts, myoblasts, astrocytes and hepatocytes). Three distinctive families of peptide ligands from malignant glioma cells were subsequently identified. Phages in these peptide ligand families demonstrated remarkable selectivity towards the target glioma cells in comparison with other tested cells. These phages were internalized by RG2 glioma cells about 63 times more efficiently than by normal brain astrocyte cells.

Figure 5:
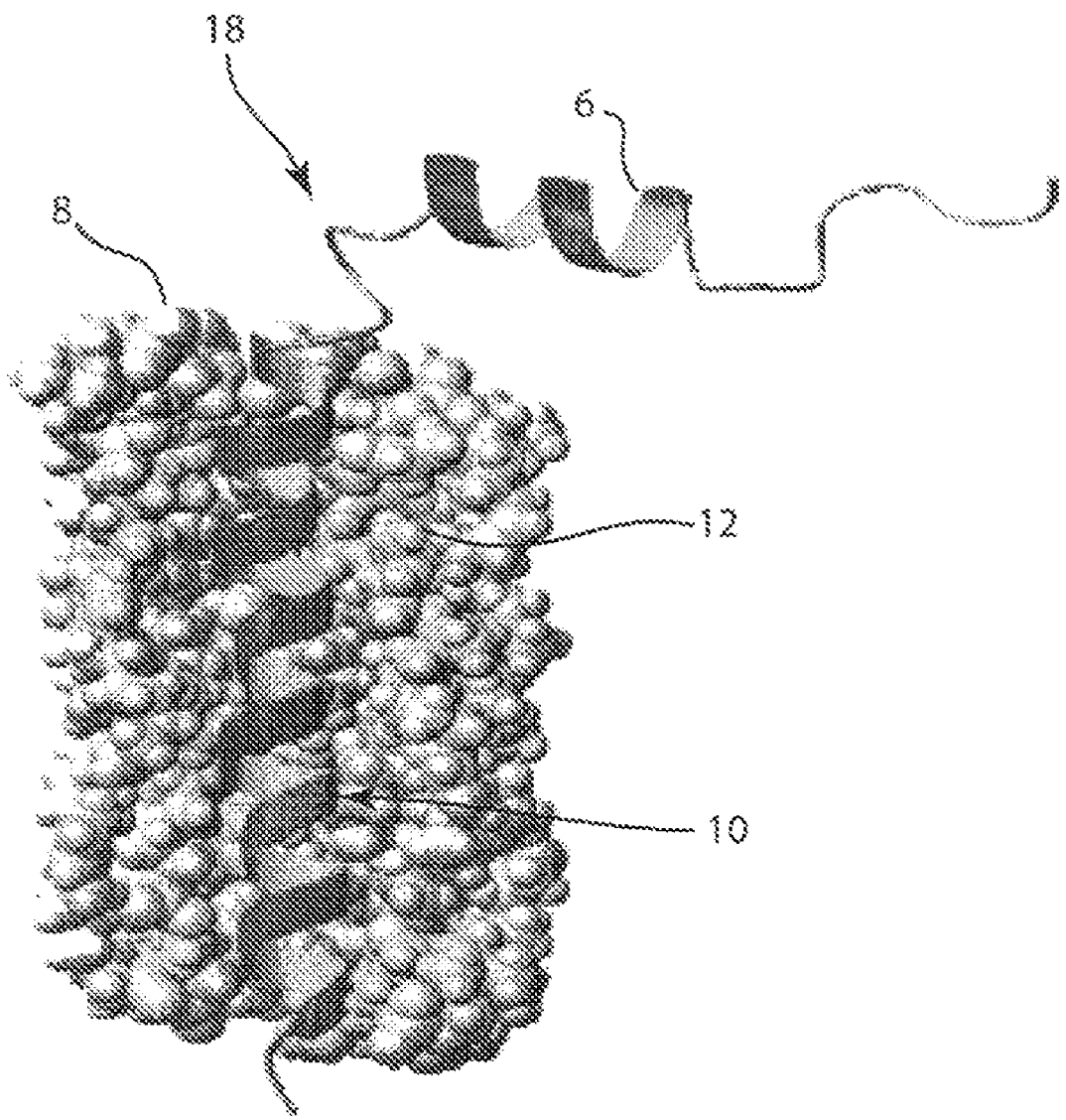
FIG. 5 is a computer model of the major coat protein pVIII 18 in a lipid environment demonstrating the trans-membrane helix 10 situated in a phospholipid bilayer 12 with an amphipathic helix 6 located near the external surface 8 of the phospholipid bilayer 12.
Figure 6:
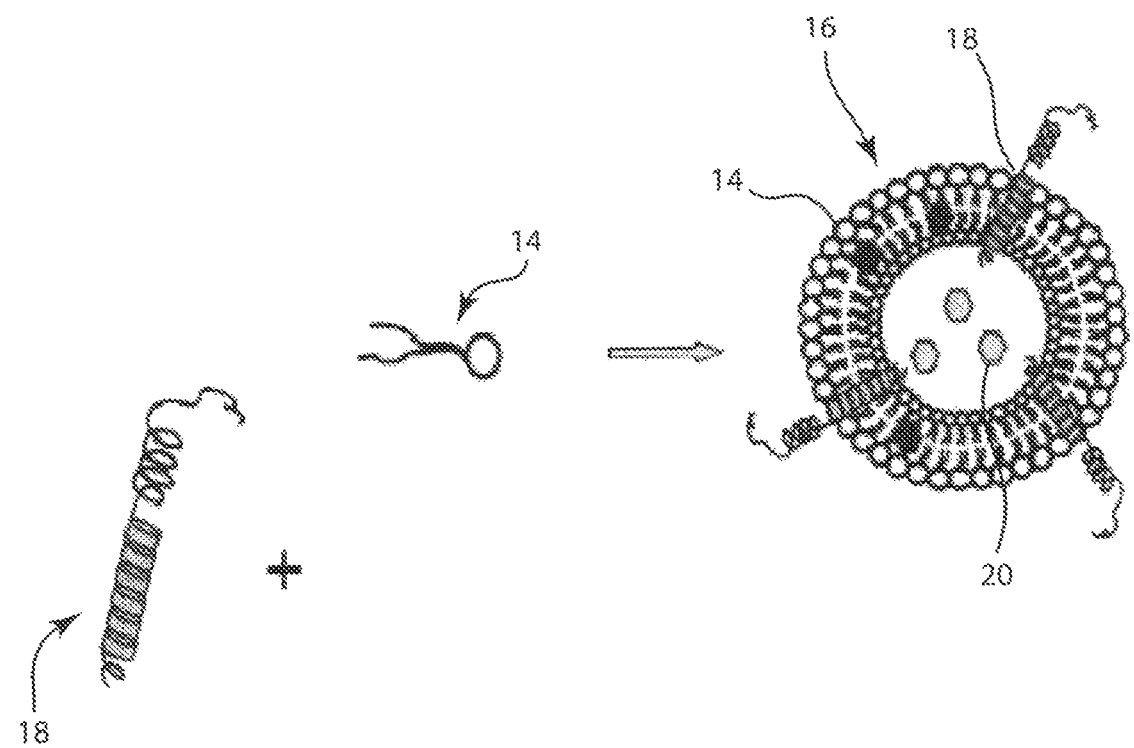
FIG. 6 is a schematic of a drug loaded liposome 16 comprising of a plurality of amphipathic molecules 14 and targeted by a pVIII protein 18. The hydrophobic helix of the pVIII protein spans the lipid layer and binding peptide is displayed on the surface of the carrier particles. The drug molecules 20 are shown as hexagons.

Referring to FIG. 6, the present disclosure contemplates a novel nanocarrier 16 using the aforementioned selected landscape phage proteins 18 as targeting mechanisms on drug delivery nanocarriers 16 having specificity and selectivity in binding to a target site. The targeted drug delivery nanocarrier 16 is comprised of a plurality of amphipathic molecules 14, a targeting landscape phage protein assembly 18, and a plurality of drug molecules 10. The amphipathic molecules 14 form a carrier particle, such as a micelle or liposome, and the drug molecules 20 are contained therein. The targeting landscape phage protein assembly 18 is complexed to the carrier particle as demonstrated in FIGS. 5 and 6. Referring to FIG. 5, and as set forth above, the targeting landscape phage protein assembly 18 can display a binding peptide on the amphipathic helix 6 that is selected to specifically and selectively bind to a target site, such as a tumor site or any other type of tissue. The landscape phage protein assembly is preferably derived from a filamentous bacteriophage fd or f8/8, but may be any bacteriophage capable of providing selectivity and specificity in binding to target sites and also capable of easily complexing with carrier particles such as micelles or liposomes. The bacteriophage that provides the protein assembly and that is complexed with the carrier particles is preferably selected using a biased selection scheme wherein the landscape phage libraries are first depleted against normal cells and then selected for binding affinity to the targeted tissues. See, also, Samoylova et al, Molecular Cancer Therapeutic 2, 1129-1137 (2003); and Romanov et al, Prostate 47(4), 239-251 (2001).

It is contemplated that any type of drug molecules desired to be delivered to a specific target site may be contained within the carrier particle. Anti-cancer drug molecules, antibiotic drug molecules and therapeutic polynucleotides are just a few examples of the type of drug molecules that may be contained within the targeted drug delivery nanocarrier disclosed herein. Specific, non-limiting, examples of drugs contained in the targeted drug delivery of nanocarriers of this disclosure include doxorubicin, paclitaxel, caelyx and carboplatin.

The present disclosure also contemplates a method for forming a targeted drug delivery nanocarrier. In this method, a plurality of bacteriophage displaying a binding peptide for a desired target site are obtained, the bacteriophage are then treated with a denaturing agent and then subsequently mixed with a plurality of carrier particles. During the mixing, the bacteriophage are complexed to the carrier particles as further described herein. The mixture is then purified to obtain a plurality of drug delivery nanocarriers. In this method, the bacteriophages are selected as discussed above.

The step of treating the plurality of bacteriophage with a denaturing agent preferably includes treating the bacterial phase with chloroform to result in a stripped phage. The stripped phage is a composition of disassembled phage coat proteins with 98% recombinant major coat protein pVIII forming bioselective vesicles with a unique landscape of target binding peptides. The stripped phages, after treatment with the denaturing agent, result in spheroid particles capable, in and of themselves, of binding to target cells. It was surprisingly found by the inventors that a combination of the stripped phages with carrier particles, such as micelles or liposomes, results in efficient complexing of the bacteriophage with the carrier particles without the necessity of sonification or dialysis. The resultant mixture can then be purified, for example, using filtration chromatography, to provide a plurality of targeted drug delivery nanocarriers. Accordingly, it was surprisingly found that stripped phage proteins when mixed with carrier particles such as micelles or liposomes, have efficient self-assemblage mechanisms that allow targeted drug delivery nanocarriers to be assembled effectively and efficiently.

The subject matter of the present application is further illustrated by the following examples that in no way should be construed as further limiting. The contents of all cited references and patents cited throughout this application are hereby incorporated by reference.

Experimental Results

Figure 7:
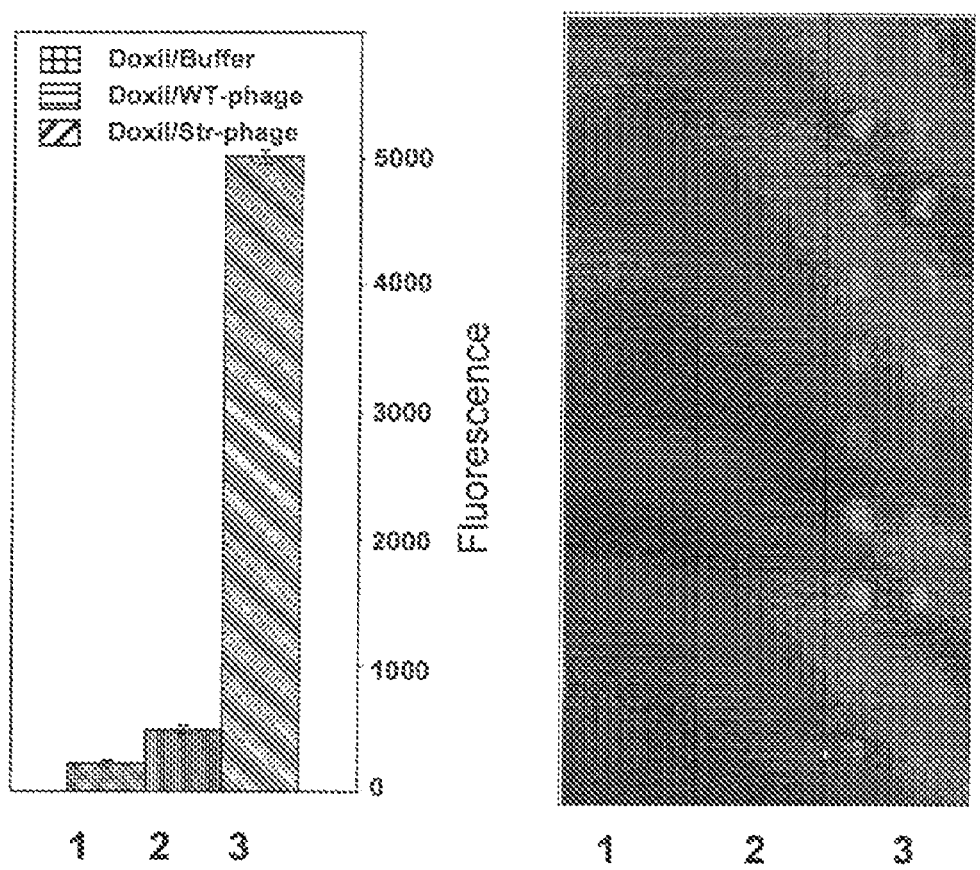
FIG. 7 is a bar graph demonstrating the relative affinity of a targeted liposome having a binding affinity for s streptavidin versus a liposome treated with a buffer and a liposome complex with a wild-type phage. The graph demonstrates the high specificity and selectivity of the targeted nanocarriers disclosed herein.

Using the intrinsic mechanism of fusion of the phage proteins with lipid membranes, we incorporated streptavidin-targeted proteins into the commercially available Doxil® liposomes. The streptavidin-binding landscape phage was affinity selected from 9-mer landscape library. The phage was converted into spheroids with chloroform and incubated with Doxil to allow fusion of the phage proteins with liposome membrane, as illustrated by FIGS. 5 and 6. As a result of the phage fusion, the liposome acquired a new emergent property—ability to bind streptavidin and streptavidin-conjugated fluorescent molecules, as was evidenced by protein microarrays (FIG. 7), fluorescent microscopy and fluorescence-activated cell sorting (FACS). The targeted and control liposomes were incubated with streptavidin-coated chips, washed and scanned (FIG. 7), or mixed with Texas Red-conjugated streptavidin (TRS), washed and analyzed by fluorescent microscopy and FACS. Complex of the modified Doxil with the target streptavidin demonstrated 50-fold higher fluorescence than pure Doxil and 10-fold higher fluorescence than control Doxil treated with TRS, as registered by FL6 channel specific for fluorescence of the Texas Red label. No significant changes of fluorescent signals were registered in the FL2 channel, more specific for doxorubicin. Complex of the targeted Doxil liposomes with streptavidin-coated gold beads was visualized by transmission electron microscopy.

Thus, we have in our possession well-developed technologies of selecting phage proteins and their transformation into targeted nanoparticulate drugs carriers.

Methods and Materials

Phage libraries and selection procedures. Protocols for selection of the cancer cell-binding and cell-penetrating phage, are known and will be applied without significant modifications, see, Romanov et al, supra (2001), Samoylova et al, supra (2003). The selection begins with depletion of phage clones binding to plastic. An aliquot of the primary phage display library is added to an empty flask (depletion flask) and incubated for 1 h at room temperature. Phage that does not bind to plastic is transferred from the depletion flask to a flask containing non-target cells to deplete phage clones that bind to common receptors of various targets.

For retrieval of target-bound phage, preparations are treated with acid elution buffer. The eluate is removed from the flask, neutralized and phage is concentrated by centrifugation in Centricone 100 kDa unit. To recover cell-penetrating phage, cells are scraped from the flask, pelleted by centrifugation and lysed in 2% sodium deoxycholate buffer. Both phage fractions (eluted and lysis) obtained sequentially from the same flask are amplified separately in the host bacteria (*E. coli*) and used in subsequent rounds of selection for the tumor cell recognition. The remaining rounds of selection are accomplished according to procedures described above, but without negative selection steps on plastic and normal cells. Phage input/output ratio may be followed by phage tittering during the selection. An increase of the ratio would indicate that the selection is specific.

Following the 4-6th round of selection, phage DNAs are amplified by PCR and sequenced to reveal peptides responsible for binding to the targets. Specificity of the selected candidate phage clones may be confirmed by a phage binding assay in comparison with a control vector phage. Briefly, cells are grown in 25 cm$^2$ flasks for approximately 48 h to subconfluence. Each phage clone is added to the cell organelles and incubated for 1 h at room temperature. The media with unbound phage is removed from the flasks, and cells will be washed eight times with cold washing/blocking buffer. Bound phage are eluted, cells are lysed and processed as above. The yield of the phage is expressed as a ratio of output to input phage titers determined by infection of the host *E. coli* bacteria.

Preparation of targeted liposomes. As loads for the targeted liposomes, doxorubicin (DOX)—cytotoxic anthracycline antibiotic isolated from *Streptomyces peucetius* var. *caesius* was initially chosen. DOX is one of the most commonly used drugs for treatment of both hematological and solid tumors, including human prostate cancer. Liposomes targeted to the cancer cells are prepared from the phages obtained as outlined above. Phages are chosen from a list of selected candidates using criteria of maximum affinity and selectivity. Four liposomes loaded with doxorubicin and targeted with cell-binding and cell-penetrating phage proteins are synthesized, purified and characterized. Control carriers without drugs contain the same composition of the lipids and phage proteins as the drug-loaded particles. Two major approaches may be utilized for obtaining the targeted drug forms: (a) fusion of the phage proteins with preformed encapsulated drug preparations, such as Doxil—doxorubicin-loaded longcirculating PEGylated STEALTH® liposomes; and (b) loading of doxorubicin into the liposomes preformed by assemblage with phage proteins. The first approach allows a fast outcome of the targeted preparations, while the second helps to optimize the drug formulations and technology of their preparation, and allows obtaining control vesicles loaded with phage proteins without drugs. This step includes physico-chemical characterization of selected drug-loaded nanoparticulates.

The targeted major coat proteins for these experiments are obtained by striping the selected phages with chloroform. Doxil® molecules are conjugated with pVIII proteins by incubation of the stripped phage (in the form of spheroids) with Doxil in the presence of mild detergent, such as octylglycoside. Following the incubation, the remaining detergent and free, non-incorporated proteins and DNA are removed by chromatography on hydroxyapatite. Liposomes may be formed by the following general methods known in the art: (a) Hydration (vortexing-extruding); (b) Detergent dialysis method; and (c) Freeze-thawing method. Liposome size distribution is determined by electron microscopy and the dynamic light scattering (NICOMP 380 Dynamic Light Scattering). Incorporation of the coat protein into the liposomes and homogeneity of the sample is controlled by Western blot and ultracentrifugation in a linear 0-40% w/w sucrose gradient. Sample homogeneity is checked in the presence of octadecyl Rhodamine B, enabling the visualization of the lipid-protein complexes. Lipid/peptide ratios in the purified vesicles will be determined according to established procedures.

Those skilled in the art will recognize, or will be able to ascertain using no more than routine experimentation many equivalents to the specific embodiments of the invention described herein. Such equivalents are intended to be encompassed by the following claims which particularly point out and distinctly claim the subject matter regarded as the invention.

What is claimed is:

1. A targeted drug delivery nanocarrier, the nanocarrier comprising: a plurality of phospholipid molecules; a targeting landscape phage protein assembly that is denatured and has a spheroid conformation; and a plurality of drug molecules; wherein the phospholipid molecules form a liposome comprising a phospholipid bilayer having the drug molecules contained therein and the targeting landscape phage protein assembly is complexed to the liposome via self-assembly and proteins of the targeting landscape phage protein assembly are oriented with their N-terminus on the surface of the liposome and their C-terminus in the interior of the liposome and wherein the targeting landscape phage protein assembly displays a binding peptide on the surface of the liposome that is selected to specifically and selectively bind to a target site, and wherein the landscape phage protein assembly is a filamentous bacteriophage coat protein assembly that displays the binding peptide in a pVIII major coat protein.

2. The targeted drug delivery nanocarrier of claim 1, wherein the drug molecules are anti-cancer drug molecules.

3. The targeted drug delivery nanocarrier of claim 1, wherein the drug molecules are antibiotic drug molecules.

4. The targeted drug delivery nanocarrier of claim 1, wherein the drug molecules are therapeutically active polynucleotides.

5. The targeted drug delivery nanocarrier of claim 2, wherein the drug molecules are doxorubicin, paclitaxel, caelyx or carboplatin.

6. A targeted drug delivery nanocarrier, the nanocarrier comprising: a plurality of phospholipid molecules; a plurality of recombinant filamentous bacteriophage pVIII major coat proteins; and a plurality of drug molecules; wherein the phospholipid molecules form a liposome comprising a phospholipid bilayer and having the drug molecules contained therein and the targeting landscape phage proteins are complexed to the liposome via self-assembly and the targeting landscape phage proteins are oriented with their N-terminus on the surface of the liposome and their C-terminus in the interior of the liposome and wherein the plurality of recombinant filamentous bacteriophage pVIII major coat proteins display a binding peptide on the surface of the liposome that is selected to specifically and selectively bind to a target site.

7. The targeted drug delivery nanocarrier of claim 6, wherein the drug molecules are anti-cancer drug molecules.

8. The targeted drug delivery nanocarrier of claim 7, wherein the drug molecules are doxorubicin, paclitaxel, caelyx or carboplatin.

9. The targeted drug delivery nanocarrier of claim 6, wherein the drug molecules are antibiotic drug molecules.

10. The targeted drug delivery nanocarrier of claim 6, wherein the drug molecules are therapeutically active polynucleotides.

* * * * *